United States Patent [19]

Fischer

[11] 3,963,477

[45] June 15, 1976

[54] HERBICIDAL MIXTURES OF S-HALOBENZYL-N,N-DIALKYLTHIOLCARBAMATES AND 3-LOWER ALKYL-2,1,3-BENZOTHIADIAZINONE-(4)-2,2-DIOXIDES AND SALTS THEREOF

[75] Inventor: Adolf Fischer, Mutterstadt, Germany

[73] Assignee: Badische Anilin- & Soda-Fabrik Aktiengesellschaft, Ludwigshafen (Rhine), Germany

[22] Filed: Feb. 19, 1975

[21] Appl. No.: 551,129

Related U.S. Application Data

[62] Division of Ser. No. 343,347, March 21, 1973, abandoned.

[30] Foreign Application Priority Data

Apr. 13, 1972   Germany............................ 2217721

[52] U.S. Cl. ....................................... 71/91; 71/100
[51] Int. Cl.² ............................................. A01N 9/12
[58] Field of Search ................................. 71/91, 100

[56] References Cited

UNITED STATES PATENTS

| | | | |
|---|---|---|---|
| 3,671,216 | 6/1972 | Kado et al. ............................ | 71/100 |
| 3,682,616 | 8/1972 | Kimura et al. ........................ | 71/100 |
| 3,708,277 | 1/1973 | Zeidler et al. ......................... | 71/91 |
| 3,746,532 | 7/1973 | Kimura et al. ........................ | 71/100 |

OTHER PUBLICATIONS

Fischer I, "Herbicidal Compositions" (1971) ca74, No. 110714w, (1971).
Fischer II, "Herbicidal Compositions, etc.," (1971) ca75, No. 75217h, (1971).

*Primary Examiner*—Glennon H. Hollrah
*Attorney, Agent, or Firm*—Johnston, Keil, Thompson & Shurtleff

[57] ABSTRACT

Herbicidal compositions embodying mixtures of S-halobenzyl-N,N-dialkylthiolcarbamates and 3-lower alkyl-2,1,3-benzothiadiazinone-(4)-2,2-dioxides and salts thereof in weight ratios of 1:5 to 5:1.

3 Claims, No Drawings

HERBICIDAL MIXTURES OF S-HALOBENZYL-N,N-DIALKYLTHIOLCARBAMATES AND 3-LOWER ALKYL-2,1,3-BENZOTHIADIAZINONE-(4)-2,2-DIOXIDES AND SALTS THEREOF

This is a division, of abandoned application Ser. No. 343,347 filed Mar. 21, 1973.

The present invention relates to the control of unwanted plants in important agricultural crops with a herbicidal composition or by first treating the soil before emergence of the plants and subsequently treating the plants after emergence.

It is known that substituted thiolcarbamates, diphenyl ethers, acid amides, benzoic acid, carbamates, terephthalates and benzothiadiazinones have a herbicidal action. However, their action is poor.

I have now found a process for controlling the growth of unwanted plants wherein the plants are treated post-emergence with a composition of a. a compound of the formula

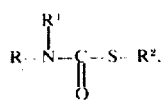

where R denotes bicycloheptyl, cyclohexyl or lower alkyl (methyl, propyl), $R^1$ denotes lower alkyl, and $R^2$ denotes lower alkyl, or allyl substituted by halogen, or benzyl substituted by halogen, b. a compound of the formula

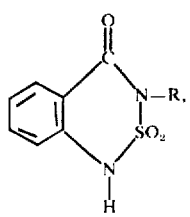

where R denotes lower alkyl of a maximum of 4 carbon atoms, or its salts, such as alkali metal, alkaline earth metal, ammonium, hydroxyalkylammonium, alkylammonium and hydrazine salts, e.g., salts of sodium, lithium, potassium, calcium, iron, methylammonium, trimethylammonium, ethylammonium, diethanolammonium, ethanolammonium, dimethylamine, dimethylethanolamine, hydrazine or phenylhydrazine.

Active ingredients a, and b may be applied in amounts of from 0.5 to 5 kg/hectare. In the composition the weight ratio may vary from 1:5 to 5:1, particularly 1:3 to 3:1.

This process and the compositions of the invention destroy unwanted plants without damaging crop plants; they are therefore particularly suitable for controlling unwanted plants (dicotyledonous seed weeds, monocotyledonous grassy seed weeds, Cyperaceae) in crop plants (rice, ground-nuts, cotton, Indian corn, soybeans, peas, beans, potatoes, cereals, alfalfa, clover).

The active ingredients may be used as solutions, emulsions, suspensions, oil dispersions, granules or dusts. The form of application depends entirely on the purpose for which the agents are being used; in any case it should ensure a fine distribution of the active ingredient.

For the preparation of solutions to be sprayed direct, mineral oil fractions having a medium to high boiling point, such as kerosene and diesel oil, further coal-tar oils and oils of vegetable and animal origin, and cyclic hydrocarbons such as tetrahydronaphthalene and alkylated naphthalenes are suitable.

Aqueous formulations may be prepared from emulsion concentrates, pastes or wettable powders by adding water. To prepare emulsions the ingredients as such or dissolved in a solvent may be homogenized in water or organic solvents by means of wetting or dispersing agents, e.g., polyethylene oxide adducts. Concentrates which are suitable for dilution with water may be prepared from active ingredient, wetting agent, adherent, emusifying or dispersing agent and possibly solvent. Oils of various types may be added to ready-to-use spray liquors.

Dusts may be prepared by mixing or grinding the active ingredients with a solid carrier, e.g., kieselguhr, talc, clay or fertilizers.

Granules may be prepared by bonding the active ingredients with solid carriers.

Oils may be used to produce directly sprayable dispersions.

The new compounds may be mixed with fertilizers, insecticides, fungicides or herbicides.

EXAMPLE 1

An agricultural plot was sown with rice (Oryza sativa), barnyard grass (Echinochloa crus-galli), yellow nutsedge (Cyperus esculentus) and waterplantain (Alisma plantago-aquatica). Treatment with the active ingredients:

I 4'-nitro-2,4-dichlorodiphenyl ether, 2 kg per hectare;
II 4'-nitro-2,4,6-trichlorodiphenyl ether, 2 kg per hectare;
III 2,4'-dinitro-4-trifluoromethyldiphenyl ether, 2 kg per hectare;
IV S-(4-chlorobenzyl)-N,N-diethylthiolcarbamate, 0.25, 0.75 and 3 kg per hectare;
V O,S-dimethyltetrachlorothioterephthalate, 2 kg per hectare;
VI methyl-2,3,5,6-tetrachloro-N-methoxy-N-methyl-terephthalamate, 3 kg per hectare;
VII 3-isopropyl-2,1,3-benzothiadiazinone-(4)-2,2-dioxide, 0.25, 0.5, 0.75, 1.0 and 1.5 kg per hectare;
VIII 2,4-dichloro-4'-nitro-3'-methoxydiphenyl ether, 0.25, 0.5, 0.75 and 1.0 kg per hectare;
IX 3-(2-methylphenoxy)-pyridazine, 0.25, 0.5, 0.75 and 1.0 kg per hectare;
X 2,5-dichloro-6-fluorophenyl-4-nitrophenyl ether, 0.25, 0.5, 0.75 and 1.0 kg per hectare, each active ingredient being dispersed in 500 liters of water per hectare, was carried out as follows:

A with I, II, III, IV, V, VI and VII before or shortly after sowing;
B with I, II, III, IV, V, VI and VII after emergence of the weeds;
C with I, II, III, IV, V and VI before or after sowing combined with VII applied after emergence of the weeds;
D with the compositions IV+VII, VII+VIII, VII+IX and VII+X of the broadleaved and grassy weeds in the early (0 to 2nd) leaf stage.

The results obtained with these 4 treatment methods are given below:

Method

| Active ingredient | A | | | | | | | B | | | | | | |
|---|---|---|---|---|---|---|---|---|---|---|---|---|---|---|
| | I | II | III | IV | V | VI | VII | I | II | III | IV | V | VI | VII |
| Oryza sativa | 10 | 0 | 10 | 5 | 5 | 5 | 0 | 40 | 10 | 10 | 5 | 20 | 20 | 0 |
| Echinochloa crus galli | 80 | 80 | 95 | 100 | 95 | 100 | 0 | 80 | 80 | 80 | 40 | 55 | 90 | 5 |
| Cyperus esculentus | 10 | 0 | 40 | 0 | 0 | 20 | 0 | 40 | 40 | 60 | 10 | 0 | 10 | 85 |
| Alisma plantago-aquatica | 10 | 10 | 25 | 30 | 5 | 45 | 5 | 40 | 20 | 35 | 5 | 10 | 50 | 90 |

| Active ingredient | C | | | | | |
|---|---|---|---|---|---|---|
| | I+VIII | II+VIII | III+VIII | IV+VIII | V+VIII | VI+VIII |
| Oryza sativa | 10 | 0 | 10 | 5 | 5 | 5 |
| Echinochloa crus-galli | 90 | 90 | 100 | 100 | 100 | 100 |
| Cyperus esculentus | 95 | 95 | 100 | 85 | 85 | 100 |
| Alisma plantago-aquatica | 100 | 100 | 100 | 100 | 100 | 100 |

| Active ingredient kg/ha | D | | | | | |
|---|---|---|---|---|---|---|
| | IV | | VII | | VII | |
| | 0.75 | 0.25 | 0.75 | 0.25 | 0.5 | 1.0 |
| Oryza sativa | 5 | 0 | 0 | 0 | 0 | 0 |
| Echinochloa crus-galli | 65 | 45 | 8 | 0 | 6 | 15 |
| Cyperus esculentus | 20 | 5 | 65 | 50 | 60 | 70 |
| Cyperus rotundus | 10 | 5 | 60 | 45 | 50 | 70 |
| Scirpus maritimus | 20 | 10 | 60 | 40 | 50 | 70 |
| Scirpus mucronatus | 25 | 10 | 65 | 50 | 55 | 70 |
| Alisma plantago-aquatica | 15 | 5 | 50 | 35 | 40 | 60 |
| Butomus umbellatus | 5 | 0 | 60 | 40 | 45 | 65 |
| Ammannia coccinea | 15 | 5 | 55 | 40 | 50 | 60 |
| Ammannia auriculata | 10 | 5 | 60 | 45 | 50 | 65 |

| Active ingredient kg/ha | VIII | | | |
|---|---|---|---|---|
| | 0.25 | 0.5 | 0.75 | 1 |
| Oryza sativa | 5 | 7 | 8 | 10 |
| Echinochloa crus-galli | 40 | 45 | 55 | 60 |
| Cyperus esculentus | 10 | 20 | 25 | 35 |
| Cyperus rotundus | 10 | 15 | 20 | 25 |
| Scirpus maritimus | 10 | 20 | 30 | 45 |
| Scirpus mucronatus | 5 | 15 | 30 | 40 |
| Alisma plantago-aquatica | 10 | 15 | 20 | 30 |
| Butomus umbellatus | 5 | 8 | 10 | 15 |
| Ammannia coccinea | 10 | 12 | 15 | 20 |
| Ammannia auriculata | 0 | 5 | 5 | 8 |

| Active ingredient kg/ha | IX | | | |
|---|---|---|---|---|
| | 0.25 | 0.5 | 0.75 | 1 |
| Oryza sativa | 0 | 5 | 10 | 12 |
| Echinochloa crus-galli | 40 | 50 | 55 | 60 |
| Cyperus esculentus | 15 | 25 | 30 | 45 |
| Cyperus rotundus | 10 | 12 | 15 | 20 |
| Scirpus maritimus | 15 | 20 | 25 | 40 |
| Scirpus mucronatus | 5 | 15 | 20 | 30 |
| Alisma plantago-aquatica | 15 | 20 | 25 | 40 |
| Butomus umbellatus | 10 | 12 | 15 | 25 |
| Ammannia coccinea | 10 | 12 | 15 | 20 |
| Ammannia auriculata | 10 | 12 | 15 | 20 |

| Active ingredient kg/ha | X | | | | IV+VII | | |
|---|---|---|---|---|---|---|---|
| | 0.25 | 0.5 | 0.75 | 1 | 0.75+0.25 | 0.25+0.25 | 0.25+0.75 |
| Oryza sativa | 0 | 4 | 5 | 8 | 5 | 0 | 0 |
| Echinochloa crus-galli | 35 | 40 | 60 | 65 | 80 | 60 | 70 |
| Cyperus esculentus | 5 | 15 | 20 | 30 | 80 | 65 | 85 |
| Cyperus rotundus | 5 | 8 | 10 | 15 | 75 | 65 | 80 |
| Scirpus maritimus | 5 | 10 | 15 | 20 | 80 | 60 | 85 |
| Scirpus mucronatus | 10 | 15 | 20 | 30 | 85 | 70 | 90 |
| Alisma plantago-aquatica | 10 | 15 | 20 | 30 | 55 | 45 | 70 |
| Butomus umbellatus | 5 | 8 | 10 | 15 | 50 | 45 | 55 |
| Ammannia coccinea | 5 | 10 | 15 | 20 | 70 | 55 | 80 |
| Ammannia auriculata | 0 | 5 | 10 | 15 | 70 | 60 | 85 |

| Active Ingredient kg/ha | VII+VIII | | |
|---|---|---|---|
| | 0.25+0.75 | 0.25+0.25 | 0.75+0.25 |
| Oryza sativa | 8 | 5 | 5 |
| Echinochloa crus-galli | 85 | 55 | 75 |
| Cyperus esculentus | 80 | 70 | 85 |
| Cyperus rotundus | 80 | 70 | 85 |
| Scirpus maritimus | 75 | 65 | 85 |
| Scirpus mucronatus | 85 | 75 | 75 |

Method-continued

| | | | |
|---|---|---|---|
| Alisma plantago-aquatica | 65 | 55 | 75 |
| Butomus umbellatus | 70 | 65 | 80 |
| Ammannia coccinea | 60 | 65 | 85 |
| Ammannia auriculata | 70 | 65 | 70 |

| Active ingredient kg/ha | 0.25+0.75 | VII+IX 0.25+0.25 | 0.75+0.25 |
|---|---|---|---|
| Oryza sativa | 10 | 0 | 0 |
| Echinochloa crus-galli | 70 | 55 | 65 |
| Cyperus esculentus | 85 | 70 | 90 |
| Cyperus rotundus | 70 | 70 | 90 |
| Scirpus maritimus | 85 | 70 | 80 |
| Scirpus mucronatus | 85 | 70 | 80 |
| Alisma plantago-aquatica | 70 | 60 | 80 |
| Butomus umbellatus | 70 | 65 | 75 |
| Ammannia coccinea | 65 | 60 | 75 |
| Ammannia auriculata | 70 | 60 | 80 |

| Active ingredient kg/ha | 0.25+0.75 | VII+X 0.25+0.25 | 0.75+0.25 |
|---|---|---|---|
| Oryza sative | 5 | 0 | 0 |
| Echinochloa crus-galli | 75 | 45 | 70 |
| Cyperus esculentus | 80 | 65 | 85 |
| Cyperus rotundus | 70 | 60 | 80 |
| Scirpus maritimus | 70 | 50 | 80 |
| Scirpus mucronatos | 85 | 65 | 95 |
| Alisma plantago-aquatica | 70 | 60 | 85 |
| Butomus umbellatus | 65 | 50 | 70 |
| Ammannia coccinea | 60 | 50 | 65 |
| Ammannia auriculata | 70 | 55 | 80 |

0 = no damage
100 = complete destruction

The following compositions provide the same good action:

O,O-dimethyl-2,3,5,6-tetrachloroterephthalate,
2,3,5-trichloropyridinol-(4),
2,4-dichloro-4'-cyanodiphenyl ether,
2,4,6-trichloro-4'-cyanodiphenyl ether,
3-chloro-4-fluoro-4'-nitrodiphenyl ether,
3-chloro-4-bromo-4'-nitrodiphenyl ether,
3-chloro-4-methyl-4'-nitrodiphenyl ether,
3-chloro-2-fluoro-4'-nitrodiphenyl ether,
3-bromo-2-fluoro-4'-nitrodiphenyl ether,
2,4-dichloro-4'-nitrodiphenyl ether,
2,4-dibromo-4'-nitrodiphenyl ether,
2,4-dichloro-4'-nitro-3'-methoxydiphenyl ether,
2-phenoxypyridazine,
3-(2-ethylphenoxy)-pyridazine,
3-(2-propylphenoxy)-pyridazine,
3-(2-isopropylphenoxy)-pyridazine,
3-(2-sec-butylphenoxy)-pyridazine,
3-(2-tert-butylphenoxy)-pyridazine,
6-chloro-3-[2-(propenyl)-phenoxy]-pyridazine,
6-chloro3-[2-(2-methyl)-phenoxy]-pyridazine,
3-[2-(2-propyl)-phenoxy]-pyridazine,
3-(2-methyl-5-isopropylphenoxy)-pyridazine,
3-(2-isopropyl-5-methylphenoxy)-pyridazine,
3-(2-sec-butyl-5-methylphenoxy)-pyridazine,
3-(2-methyl-4-tert-butylphenoxy)-pyridazine,
3-phenoxypyridazine,
3-(2-methylphenoxy)-pyridazine,
3-(2,5-dimethylphenoxy)-pyridazine,
3-phenylthiopyridazine,
3-(2-methylphenylthio)-pyridazine,
3-(2-methylphenylthio)-6-methylpyridazine,
3-methyl-6-(2-methylphenylthio)-pyridazine,
3-(2-methyl-4-chlorophenylthio)-pyridazine,
3-(4-tert-butylphenylthio)-pyridazine
3-methyl-6-(2,4-dimethylphenylthio)-pyridazine,
3-(2,4-dichlorophenylthio)-pyridazine,
3-isopropyl-2,1,3⁺-benzothiadiazinone-(4)-2,2-dioxide.

We claim:
1. A process for controlling the growth of unwanted plants which comprises treating said plants postemergence with a herbicidally effective amount of
   a. a compound of the formula

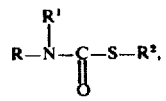

wherein R and R¹ each denote lower alkyl and R² denotes benzyl substituted by halogen, and
   b. a compound of the formula

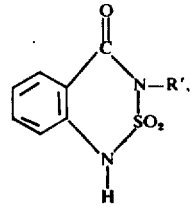

wherein R' denotes lower alkyl of a maximum of four carbon atoms or an alkali metal, alkaline earth metal, ammonium, lower alkylammonium, lower hydroxylalkylammonium, or hydrazine salt thereof, the weight ratio of a to b being in the range of 1:3 to 3:1.

2. A process as claimed in claim 1 wherein compound a is S-(4-chlorobenzyl)-N,N-diethylthiolcarbamate.

3. A process as claimed in claim 1 wherein compound a is S-(4-chlorobenzyl)-N,N-diethylthiolcarbamate, and R in compound b is isopropyl.

* * * * *